United States Patent
Morgenstern

(10) Patent No.: US 7,128,706 B2
(45) Date of Patent: Oct. 31, 2006

(54) VAGINAL PROBE; IN PARTICULAR FOR TREATING INCONTINENCE

(76) Inventor: Jürgen Morgenstern, In der Rehwiese 11, Düsseldorf (DE) 40629

( * ) Notice: Subject to any disclaimer, the term of this patent is extended or adjusted under 35 U.S.C. 154(b) by 0 days.

(21) Appl. No.: 10/508,170

(22) PCT Filed: Mar. 18, 2003

(86) PCT No.: PCT/DE03/00884

§ 371 (c)(1), (2), (4) Date: May 13, 2005

(87) PCT Pub. No.: WO03/077742

PCT Pub. Date: Sep. 25, 2003

(65) Prior Publication Data

US 2005/0228316 A1 Oct. 13, 2005

(30) Foreign Application Priority Data

Mar. 19, 2002 (DE) ................ 102 12 832

(51) Int. Cl.
*A61F 2/00* (2006.01)
(52) U.S. Cl. .................................................. 600/30
(58) Field of Classification Search ............ 600/29–32, 600/591; 128/DIG. 25; 607/138; 601/45; 73/379.01, 379.08
See application file for complete search history.

(56) References Cited

U.S. PATENT DOCUMENTS

| | | | |
|---|---|---|---|
| 6,110,099 A * | 8/2000 | Benderev | 600/30 |
| 6,394,939 B1 * | 5/2002 | Stein | 482/148 |
| 6,454,698 B1 * | 9/2002 | Forsell | 600/30 |
| 6,625,495 B1 * | 9/2003 | Alon et al. | 607/116 |
| 6,685,623 B1 * | 2/2004 | Presthus et al. | 600/29 |
| 6,905,471 B1 * | 6/2005 | Leivseth et al. | 600/591 |
| 2003/0028180 A1 * | 2/2003 | Franco | 606/14 |

FOREIGN PATENT DOCUMENTS

| | | |
|---|---|---|
| DE | 19706042 | 8/1998 |
| WO | WO0003659 | 1/2000 |

* cited by examiner

Primary Examiner—John P. Lacyk
(74) Attorney, Agent, or Firm—Akerman Senterfitt

(57) ABSTRACT

The invention relates to a vaginal probe, in particular for treating incontinence and comprising an external part (20), an internal part (22), a bridge (24) connecting said parts and processing electronics (28). The external part (20) is configured as a handle and has a cavity (26) and the internal part (22) is a body that is rounded on all sides. Said body: a) has sensors (44–51) on its surface, which are connected to the processing electronics (28); b) is symmetrical about a longitudinal central plane (32), which runs between the legs of a patient using said probe; c) has cross-sections that are perpendicular to said longitudinal central plane (32) and to the bridge (24), in which the measured height dimension H of said body, which runs parallel to the longitudinal central plane (32), is at maximum half its measured width B, which runs perpendicular to the longitudinal central plane (32); and d) has a front sub-section (36) that is at a distance from the external part (20), a central section (38) and a rear sub-section (40). Said central section (38) is curved, the rear sub-section (40) is connected to the bridge (24) and the front sub-section (36) and the rear sub-section (40) are interconnected in one piece by means of the central section (38) and are at an angle of between 170 DEG–100 DEG in relation to one another.

13 Claims, 4 Drawing Sheets

VAGINAL PROBE; IN PARTICULAR FOR TREATING INCONTINENCE

CROSS-REFERENCE TO RELATED APPLICATIONS

This application forms the national phase of PCT/DE03/00884, filed Mar. 18, 2003, which claims the benefit of German Application No. 102 12 832.4, filed Mar. 19, 2002.

BACKGROUND OF THE INVENTION

Urinary and faecal incontinence are frequent diseases the frequency of which increases with age. It is assumed that about 2% of the population suffer from urinary and/or faecal incontinence. With age, this percentage increases to more than 10%. Usually, the affected patients are using management means such as pads and diapers. In the long run, this entails considerable costs.

It is known that incontinence, more specifically stress incontinence, can be treated by training the pelvic floor muscles. Prior art vaginal probes, which are also called introitus probes, are known, said probes being introduced into the vagina and having electrodes for registering the electrical activity, what is termed the EMG signal, of the pelvic floor upon contraction of the pelvic floor muscles. These vaginal probes have also already been utilized in such a manner that their sensors, which are configured in the form of electrodes, deliver a voltage that stimulates the muscles to contract. It is also known to use vaginal probes in what are termed biofeedback applications, the reader being referred in this context to DE 19706042 C2. Hereby, the electrodes of the vaginal probe record potentials of the body. These potentials are amplified in the form of a signal that is visually or acoustically returned to the female patient. As a result, the female patient learns to selectively control her body functions on her own. This is advantageous, more specifically if the training is to be performed at home. As to prior art, the reader is generally referred to the German magazine Geburtsk. u. Frauenheilk. (obstetrics and gynecology) 58 (1998) 581 to 587 "Das Oberflächen-EMG der Beckenbodenmuskulatur (Introitus-EMG) bei kontinenten und inkontinenten Frauen" (The surface-EMG of the pelvic floor muscles (introitus-EMG) in continent and incontinent female patients).

The prior art vaginal probes are configured to exhibit rotational symmetry, meaning they have a round cross section. In this context, the reader is also referred to the already mentioned German magazine that shows an illustration of such an introitus probe. It is connectable to a control apparatus via a cable. In many models, the cross section varies over the length of the internal portion. The electrodes also exhibit rotational symmetry and are accordingly configured to be rings, longitudinal electrodes or caps. The rotary position in which these prior art vaginal probes are introduced into the vagina is no concern. These electrodes only register a mean value of the individual potentials.

The prior art vaginal probes have considerable disadvantages. As the electrodes are arranged with rotational symmetry, the various muscle groups it would be desirable to register cannot be scanned directly so that the already mentioned mean is taken over a larger sized area and, as a result thereof, in most cases over different muscle groups.

Furthermore, the previously known vaginal probes are unpractical in that, on the one side, they are connected to the control apparatus through the supply line, which is inconvenient in practical use, and that, on the other side, they are also susceptible to slip out when inserted, more specifically while walking. As a result, the use of the prior art vaginal probes in the normal home setting, be it in standing, walking or any other position, is rendered more difficult.

SUMMARY OF THE INVENTION

The vaginal probe with or without sensors can also directly serve as a pessary and, as a result thereof, for conservative treatment of stress incontinence. Such a pessary is inserted by the incontinent woman and its lower portion then exerts a mild pressure onto the urethra, said pressure increasing in stress situations (continence pessary).

The pelvic floor includes the pelvic diaphragm and the urogenital diaphragm. The pelvic diaphragm consists of striated (voluntary) muscles and of the surrounding fasciae (Fascia diaphragmatic pelvis superior et inferior). The pelvic floor muscle is made up of two components, the M. levator ani and the M. puborectalis. From a functional point of view, it makes no sense to further subdivide the M. levator ani. The M. puborectalis as sphincter pubovisceralis helps in keeping the urethra and the rectum closed.

This is where the invention comes in. It is its object to indicate a vaginal probe that is capable of adding to the patient's comfort and is more specifically manufactured in such a manner that it finds good clear hold in the vagina, meaning that it will not slip out during walking for example, and that is inserted with a clear orientation. Additionally, a development thereof should offer the possibility to selectively register the potentials of individual muscles.

This object is solved by a vaginal probe having an external portion, an internal portion, a crosspiece for joining these two portions together, with the external portion being configured as a handle and the internal portion being a generally rounded body that a) is oriented symmetrical about a longitudinal center plane that is oriented between the legs of the female patient when inserted, b) comprises across said longitudinal center plane and across said crosspiece cross sections in which its height dimension H, which is determined parallel to the longitudinal center plane, is at most half its width B, which is determined across said longitudinal center plane, and c) comprises a front subsection distal from the external portion, a central section and a rear subsection, the central section being curved, the rear subsection being connected to the crosspiece, said front subsection and said rear subsection being integrally joined together through the central section and said front subsection and said rear subsection being inclined to each other at an angle of 170°–120°.

The great advantage of this vaginal probe is that it optimally conforms to the natural shape of a vagina. It does not exhibit rotational symmetry but is substantially flat. As a result, the positioning thereof inside the vagina is imposed, the internal portion forming, in accordance with its outer shape, a volume in the vagina.

The internal portion of the vaginal probe is composed of the front subsection, the central section and the rear subsection, all of these three subsections being integrally joined together with smooth transitions. The front and the rear subsections are inclined to each other at an angle of between 180° and 100°. This conforms to the actual anatomy of a woman. (In a standing woman), the vagina first rises vertically before it bends over the pelvic diaphragm to extend as far as the spine. The rear subsection is associated with the lower vertical portion of the vagina. The front subsection is associated with the section located above the inclination described. It is not necessary to adapt the shape of the vaginal probe to the actual circumstances. The front subsection can be implemented, and is implemented, in such a manner that the internal portion is prevented as far as practicable from slipping out. It is more specifically the bend described to be provided in the internal portion that prevents the probe from slipping out as it ensures a good fit and hold. A relative large surface of the internal portion including its larger overall length as compared to prior art probes is also advantageous. A relatively large surface is thus provided for adhesion, which also prevents the probe from slipping out. The length of the introitus probe in accordance to the magazine mentioned herein above is about 60 to 65 mm. The length of the internal portion of the vaginal probe of the invention is at least one centimeter longer and typically is about 80 mm.

The internal portion of the vaginal probe in accordance with the invention is longer than the corresponding prior art apparatus, this extra length being provided by the front subsection.

Generally, the internal portion accordingly has a shape that effects a definite position within the vagina. As contrasted with the prior art probes, the internal portion will always adopt the same angular position within the vagina. If the internal portion is inserted being thereby rotated 180° relative to the right position, the female patient will easily notice and feel that it does not fit correctly because of the bend described as being provided between the front and the rear subsection. Additionally, the shape of the external portion may serve as an assistance and a guide so that the probe be inserted correctly.

In accordance with the invention, the external portion is configured as a handle. It serves to insert and to remove the internal portion. It is formed to be relatively flat so that it may be conveniently worn between the legs. Its main dimensions are in the longitudinal center plane. As a result thereof, it forms an abutment face. It is flat between the legs. As a result, it contributes to determining the correct positioning of the internal portion. It preferably accommodates the electronic circuits of the processing electronics unit and more specifically an externally rechargeable voltage supply. The external portion preferably has a clear marking and/or shape so that the female patient is clearly apprised that if she inserts the vaginal probe in this way, it will be positioned in situ being rotated 180° relative to the right position.

The crosspiece separates the external portion from the internal portion. It is clearly thinner than the two portions and quite short. The two portions are rigidly connected together through the crosspiece. In principle, it is also possible to provide a joint or a coupling in the region of the crosspiece, more specifically in the transition part to the external portion. The crosspiece is shaped like a rod, it preferably is a tube portion.

The vaginal probe of the invention is relatively comfortable to wear. It remains in place even if the patient is moving e.g., walking. Communication with a control apparatus is preferably wireless, which eliminates the need for providing a supply line between the external portion and the control apparatus and for somehow accommodating said supply line.

In a preferred development, the internal portion comprises sensors mounted to its surface. The vaginal probe preferably has a processing electronics unit, the sensors are connected to said processing electronics unit and configured as electrically conductive areas and/or as pressure sensitive areas.

Thanks to its shape that conforms to the anatomy and to the integrated sensors, the internal portion permits to selectively register individual muscles. These muscles may then be monitored and trained so that the actual muscles forming part of the pelvic floor muscles are allowed to respond and to be trained. The sensors are always placed in such a manner that they register the very muscles involved without taking the mean.

The sensors can be configured in such a manner that they are allowed to come into the best possible contact with the muscles to be registered over possible the entire surface thereof. In the longitudinal direction for example, the sensors may have a relatively long length. Other sensors are provided in other angular positions but on the same height along the longitudinal direction.

In a particularly preferred implementation, the external portion has an abutment face oriented transverse to the crosspiece, said abutment face being large enough to prevent the external portion from being inserted into the vagina. This abutment face is preferably configured to be elongate, it is located between the legs of the female patient when worn.

It has been found that it is very advantageous if the probe tapers in the region of the crosspiece. This permits to achieve clear completion of the insertion process. Furthermore, this provision has as little as possible an influence on the female anatomy. In any case, this is intended to prevent the muscle groups from being pre-stretched so that they are capable of gathering larger force during contraction.

In a particularly preferred embodiment there is provided that the internal portion and the crosspiece form a single piece molded body, that thin electrical conductor areas are deposited on this molded body, one conductor area being provided for each sensor, and that an external, surrounding layer of electrically insulating material, more specifically a varnish layer, is provided, said varnish layer covering the molded body and the conductor areas so that only the areas intended for the sensors remain uncovered and the sensors remain freely accessible from the outside.

This permits to achieve a particularly advantageous manufacturing possibility. The molded body may be hollow or solid and can be made from any insulating material.

Configuring the internal portion as a hollow body provides the advantage that the hollow body can be filled. As a result, the probe may be filled with different weights.

In another preferred embodiment, a rounded groove is provided in the rear subsection, it is oriented symmetrical about the longitudinal center plane. Sensors are also preferably disposed in the thus configured grooved portion. This permits access to the urethra muscle and provides space for the urethra.

In another preferred embodiment, the internal portion has, in the region of the rear subsection and of the central section, a left hand side and a right hand side lateral arched cavity. Lateral sensors are preferably provided in the region of these lateral cavities. Overall probe fit is improved, the probe being loaded inward rather than outward during contraction.

The concave arrangement of the lateral sensors of the vaginal probe permit intimate contact with the legs of the loop-shaped M. puborectalis independently of the width of the Hiatus levatoris at rest or during contraction. The sensors, implemented as electrodes, are suited both for derivating action potentials and for electrically stimulating the muscle to improve its force of reflex contraction. This permits to enhance the cooperation between the abdominal muscles and the pelvic floor muscles when coughing, sneezing and so on.

It has been found out that it is preferable to releasably connect the front subsection to the rear subsection. Differently configured front subsections can thus be connected to a rear subsection that remains constant. The shape of the front subsection can thus be adapted to various conditions of the individual female patient. This permits to comply with the changing conditions in one and the same female patient, changes that may occur as a result of births and descents. An electrical and mechanical coupling e.g., a plug-connection, a screw connection or a bajonet coupling may be preferably provided in the region of the crosspiece.

The front subsection preferably serves for reference and for retaining the internal portion within a vagina. In an improved implementation, it may be provided with a reference sensor.

BRIEF DESCRIPTION OF THE DRAWINGS

Further advantages and characteristics of the invention will become apparent in the remaining claims and in the following non restrictive description of an embodiment thereof, given by way of example only with reference to the drawing. In said drawing:

DETAILED DESCRIPTION OF THE INVENTION

Figure 1:
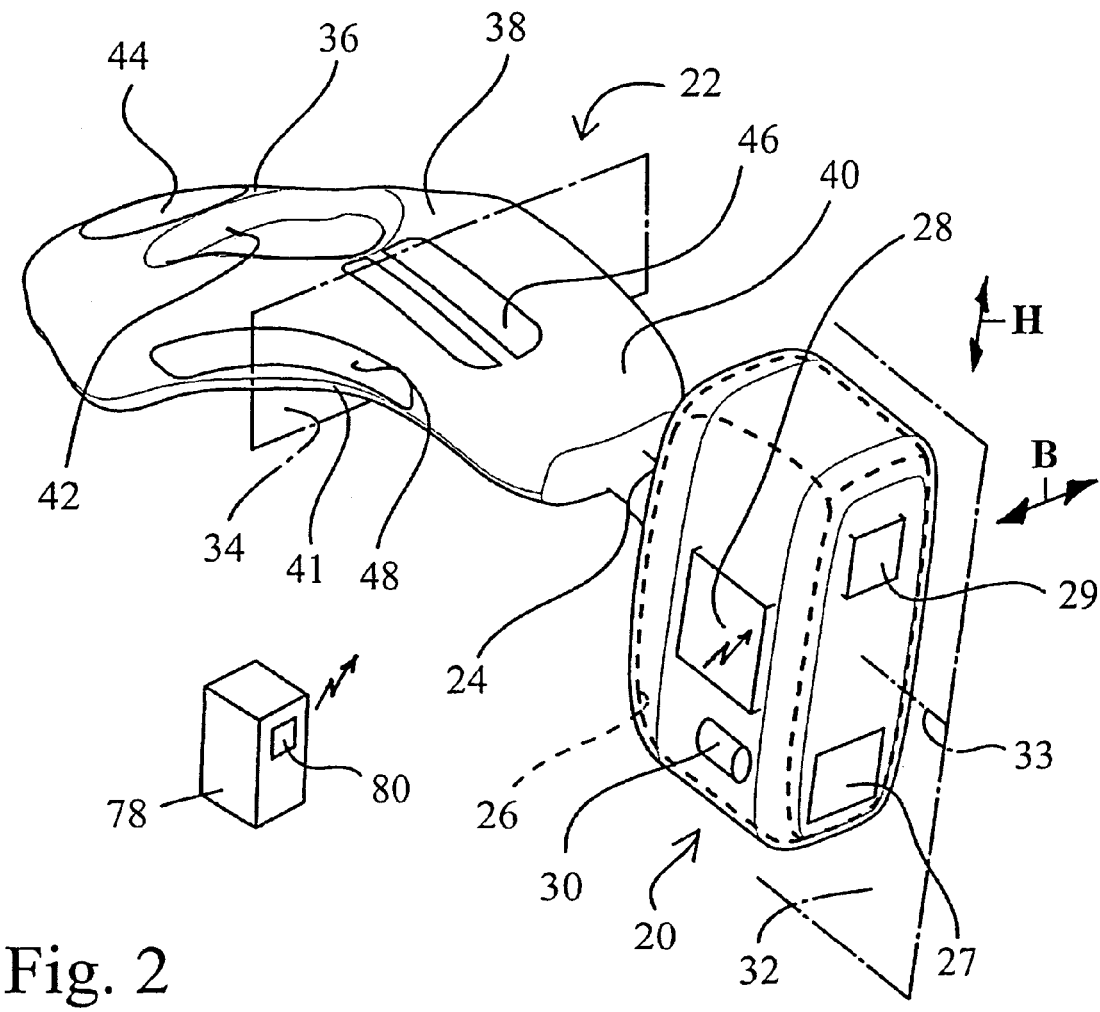
FIG. 1 is a perspective view illustrating the vaginal probe of the invention.

The vaginal probe has an external portion 20, an internal portion 22 and a crosspiece 24 that joins said two portions 20, 22 together and is configured as a short tube. The tube has a free length of about 5 to 20 mm, preferably of about 10 mm and an outer diameter of about 5 to 7 mm.

The external portion 20 is configured as a handle which is taken hold of for inserting and removing the vaginal probe. It forms a hollow space 26 for accommodating a processing electronics unit 28, a battery 30 and at need other electronic components. A three-dimensional sensor that is responsive to the earth's gravity field (e.g., ADXL 202 of Analog Devices Inc.) is integrated in a preferred embodiment. This sensor permits to continuously register the position of the vaginal probe in space and, as a result thereof, in situ. The hollow space 26 is accessible via a flap 27. Electrical external contacts 29 are provided for charging the built-in accumulators (batteries). The external portion 20 is formed substantially like a flat parallelepiped or like a cushion. It substantially consists of a thin shell so that it is as light as possible and that the hollow space 26 may be configured to be as large as possible. It is implemented so as to be quite flat for occupying but very little space between the legs. In a preferred embodiment, the external portion 20 is formed in such a manner that a clear distinction can be made between the front (in front of the legs of a female patient) and the back, exhibiting e.g., an asymmetry with regard to the crosspiece 24 in its longest extension. As a result, the female patient will understand more easily that the e.g., longer part of the external portion 20 must point vertically upward upon correct insertion of the vaginal probe.

The internal portion 22 is symmetrical about a longitudinal center plane 32. Said plane passes through the central axis 33 of the rod-shaped crosspiece 24 and extends between the legs of a female patient wearing the vaginal probe. The external portion 20 has its main dimensions in this longitudinal central plane 32. In the exemplary embodiment shown, the longitudinal central plane 32 is concurrently a plane of symmetry of the external portion 20 and of the crosspiece 24.

The internal portion 22 has cross sectional areas the cross sectional area 34 of which is shown in the Figs. This cross sectional area and all the other ones are oriented at right angles to the longitudinal center plane 32 and across the longitudinal direction of the vaginal probe. The longitudinal direction is oriented parallel to the axis 33 of the rod-shaped crosspiece 24. The cross sectional area 34 is oriented at right angles to the axis 33 of the rod-shaped crosspiece 24.

As shown in the Figs., the internal portion 22 is quite flat. It generally has a shape remotely resembling a shoespoon. The cross sectional area 34 has a height dimension H oriented in the direction of the longitudinal center plane 32 and extending across the crosspiece 24 and a width dimension B that is determined transverse to the longitudinal center plane 32. As can be seen from the Figs., the width in the region of the cross sectional area 34 is at least six times the height H. In all the possible cross sectional areas that are parallel to the cross sectional area 34, the width B is at least twice the height H. The height H is selected to be as small as possible, in the exemplary embodiment it is 10 mm maximum. The width varies between 43 and 20 mm.

Figure 2:
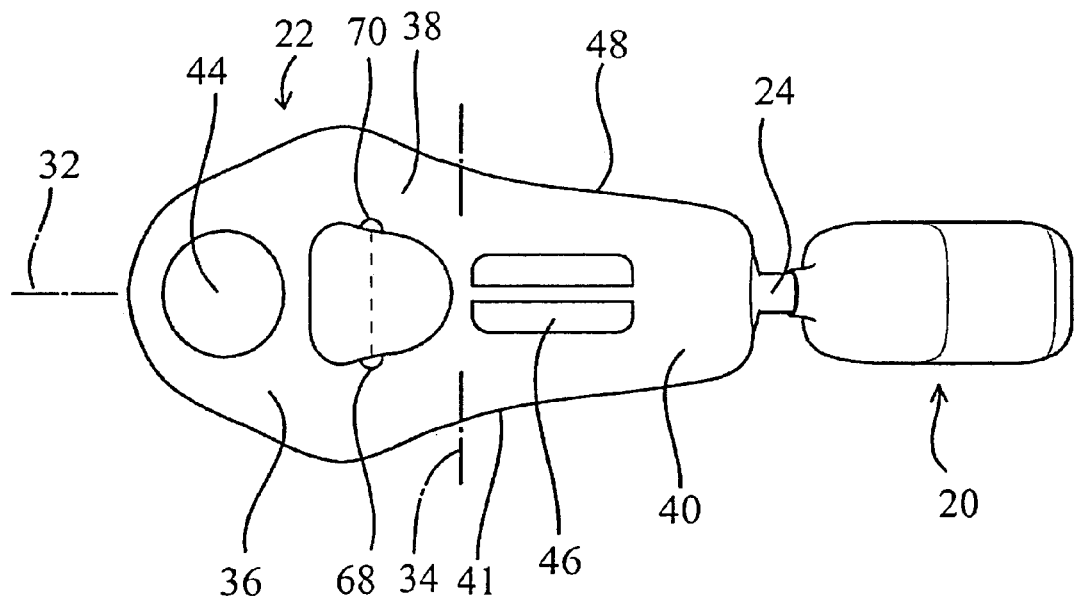
FIG. 2 is a top view of the vaginal probe.
Figure 3:
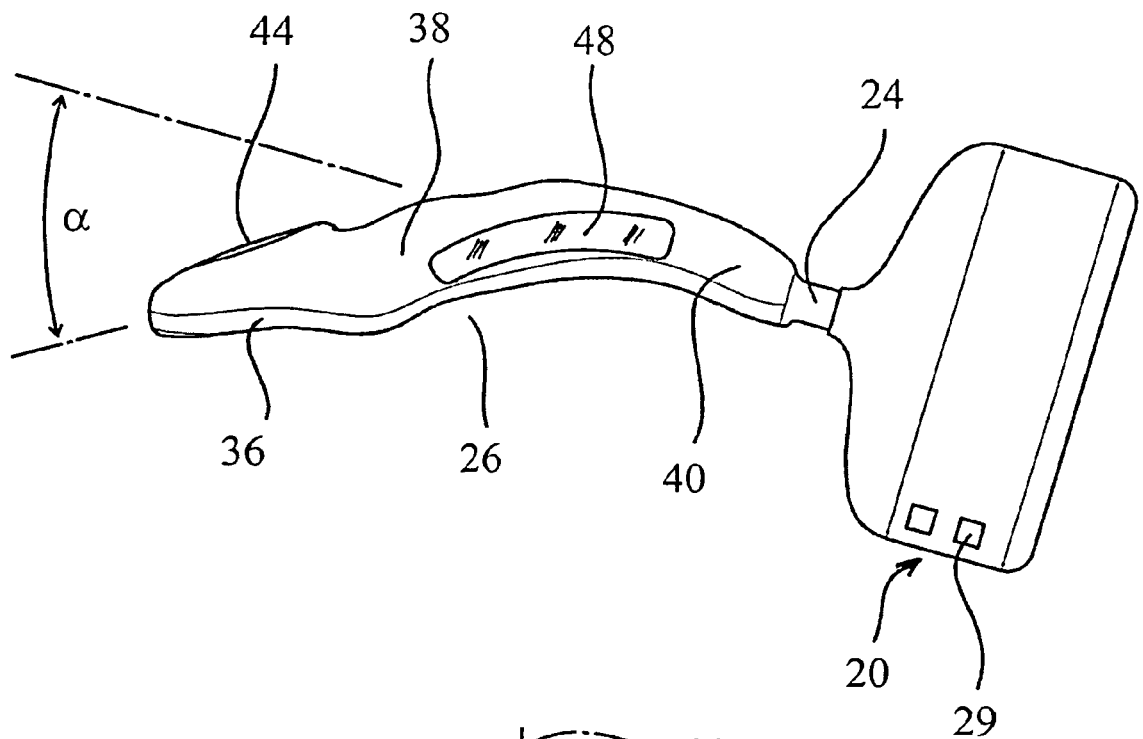
FIG. 3 is a side view of the vaginal probe.
Figure 4:
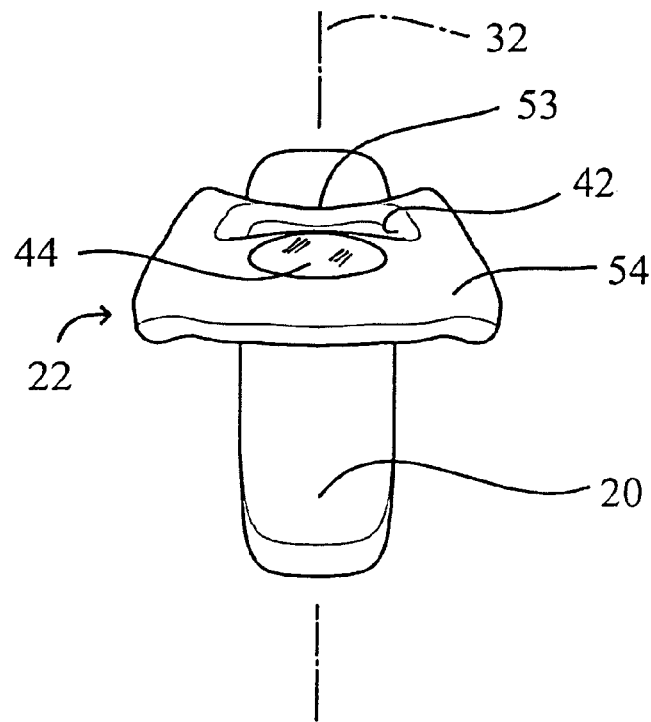
FIG. 4 is a front view of the vaginal probe, meaning a view of the front subsection.

To provide a better description, the internal portion 22 will now be divided into subsections. It has a front subsection 36, a central section 38 and a rear subsection 40 that is connected to crosspiece 24. These subsections 36 through 40 integrally merge with each other. As more specifically shown in FIG. 3, in which the longitudinal center plane 32 coincides with the plane of the paper, the rear subsection 40 is oriented substantially in the direction of the crosspiece 24. The central section 38 has a curved orientation. The front subsection 36 is inclined at an angle a of about 30° to the extended direction of the rear subsection 40 so that the angle between the front subsection 36 and the rear subsection 40 is of about 150°. In the illustration of FIG. 3, the internal portion 22 generally has approximately the shape of an arch. In the illustration in accordance with FIG. 2, in which the width dimension B lies in the plane of the drawing, the width dimension, which takes departure from the rear subsection 40, first increases on almost a straight line, passes through a respective left hand side and right hand side arched cavity 41 before decreasing again at the beginning of the front end of the central section 38, an approximately parabolic front boundary line being given thereby, see FIG. 2.

In the transition between the front subsection 36 and the central section 38 there is formed a U-shaped recess 42 that is bounded relative to the front portion 36. It has an overall area that is clearly smaller than the area defined by the outer contour in the top view of FIG. 2, the area of the recess 42 being more specifically smaller than ⅓, preferably smaller than ⅕ of the overall defined area in the top view. Given the recess 42, the probe is better retained within a vagina because tissue portions located both above and underneath partially pass through this recess and become superimposed. Therefore, in a particular implementation of the internal portion 22, an emitting diode (LED) 68 and a light sensitive receiving diode 70 are mounted into the slightly opening, U-shape oriented legs of this recess 42 in such a manner that they are located directly opposite each other on the same level so that the light absorbed by the tissue can be continuously measured for registering the oxygen saturation in the tissue. The recess 42 must not be provided, it is also possible to make a vaginal probe without said recess 42.

The sensors will now be discussed herein after. In the front subsection 36 there is provided a reference sensor 44 that is configured to be circular in the exemplary embodiment, said sensor being located between the recess 42 and the front point of the internal portion 22 and having a diameter of about 15 mm. In the embodiment shown it is located on the top side of the vaginal probe that is visible in FIG. 2. On the same side of the vaginal probe there are two oblong parallel first sensors 46. They are located in immediate proximity to the longitudinal center plane 32, in the region of a concave groove 53 and in the transition area between the rear subsection 40 and the central section 38. They form a partial grip around the urethra and are intended to register the measured signals generated by the M. sphincter urethrae externus upon contraction thereof.

Figure 5:
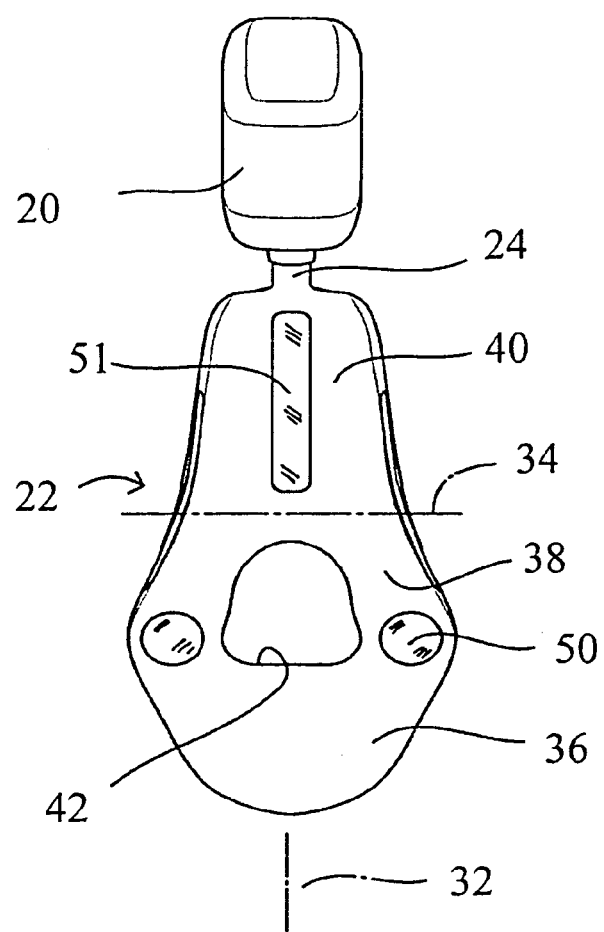
FIG. 5 is a bottom view of the vaginal probe.

In the same length position but on the side of the internal portion 22 and of the respective one of the arched cavities 41 there are disposed two second sensors 48 for scanning the M. puborectalis. These sensors are also striped and extend substantially in the longitudinal direction. Two third sensors 50 are mounted to the part of greatest width of the internal portion 22. As can be seen from FIG. 5, they are located on the bottom side of the internal portion 22. They are located on either side of the recess 42 and have a circular shape with a diameter of about 8 mm. They are associated with the pelvic floor muscles. In the rear subsection 40, there is disposed a fourth sensor 51 which extends symmetrically substantially in the longitudinal direction to the longitudinal center plane 32, said sensor coming to rest against the Pars profunda of the M. sphincter ani externus, see FIG. 5.

Accordingly, the sensors 46–50 are provided in pairs, the sensor 51 and the reference sensor 44 being single sensors. All of the sensors 44–51 are disposed and configured so as to be symmetrical to the longitudinal center plane 32. The sensors of the same type, meaning for example the first two electrodes 46 and so on, are respectively built according to the same principle.

A possible construction of the vaginal probe will be explained herein after with the help of the FIGS. 6–8. According to these, the internal portion 22 has an inner part 52 carrying the sensors 44–51 and their supply lines 58 as well as a body 54, which is formed around said inner part 52 and is connected thereto, said body being preferably manufactured by injection molding or any other casting process and surrounding the inner part 52 except for the surfaces of its sensors 44–51. The surfaces of the sensors 44–51 are flush with the surface of the body 54. For making this body 54, a suited plastic material exhibiting good adhesion to the body tissue is selected. Appropriate plastic materials are those tolerated by the body such as silicone, polyethylene, acrylate and so on, in any case insulators.

Figure 6:
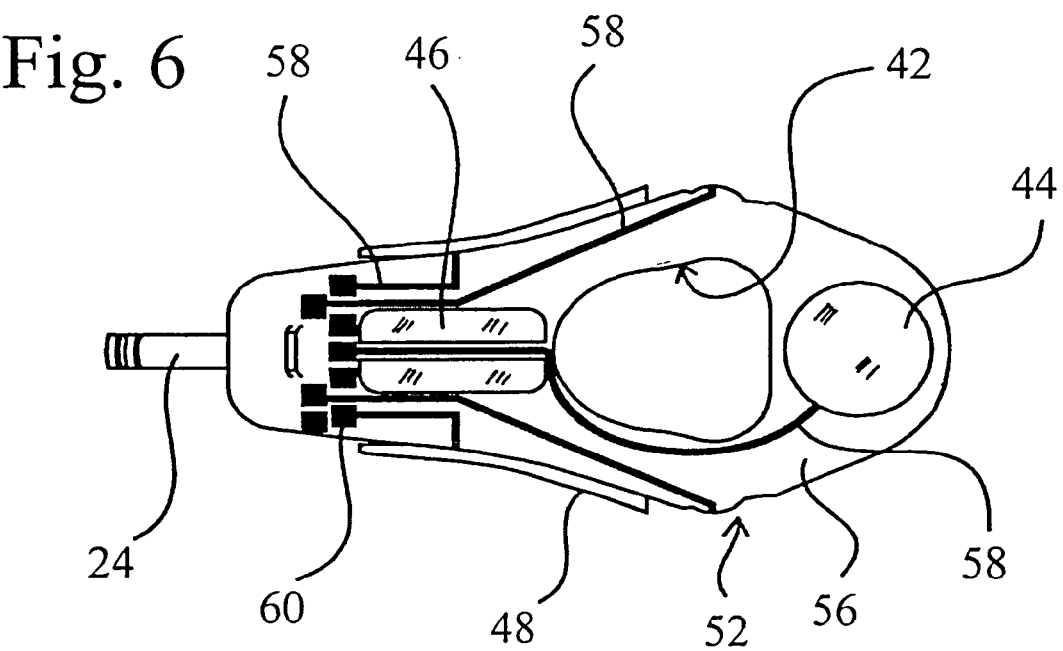
FIG. 6 is a top view of an internal portion of the vaginal probe viewed like in FIG. 2.
Figure 7:
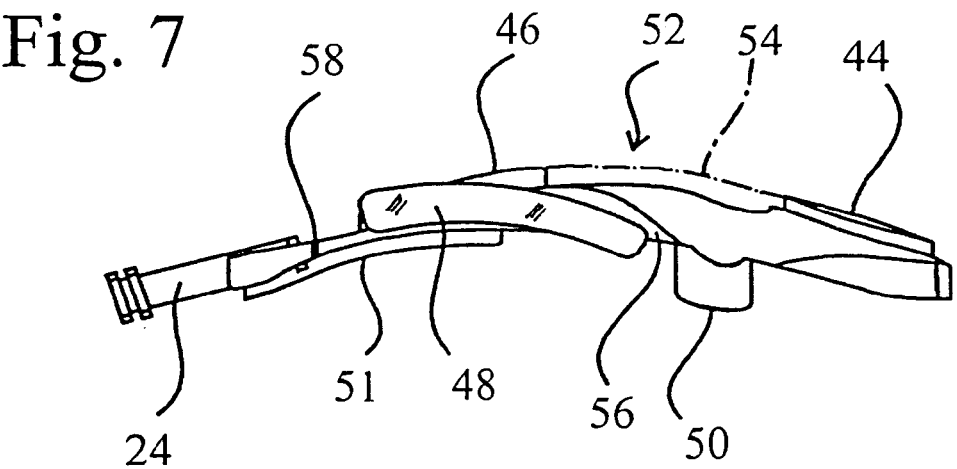
FIG. 7 is a side view of the internal portion according to FIG. 6 viewed like in FIG. 3.
Figure 8:
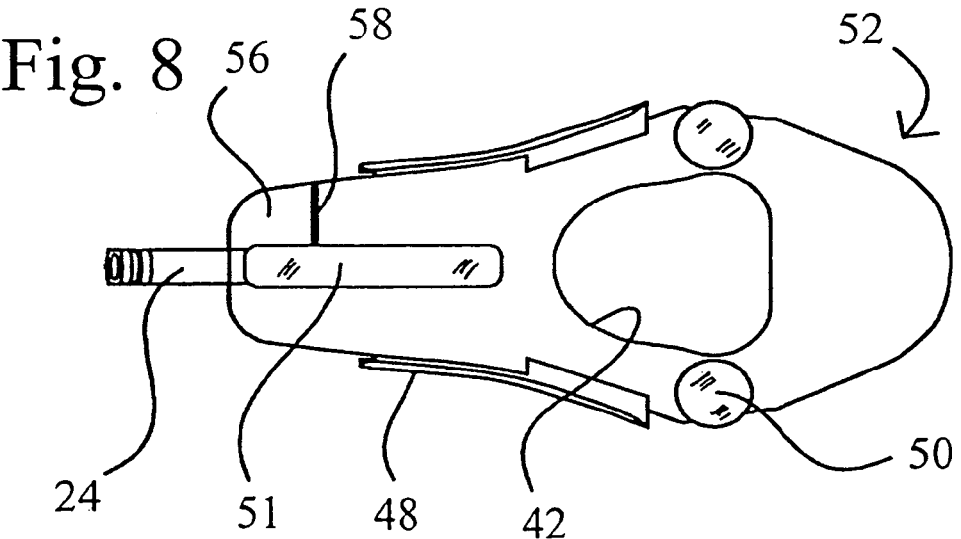
FIG. 8 is a bottom view of the internal portion according to FIG. 6 viewed like in FIG. 5.

As shown in the FIGS. 6–8, the inner part 52 consists of a flat carrier 56 and of the sensors 44–51 connected thereto. The carrier 56 is flat and has substantially the shape of the internal portion as viewed from the top (see FIG. 5) with slightly reduced dimensions though so that the body 54 is allowed to surround the carrier 56 with a wall of at least some millimeters thick. With their free surfaces which are visible from the top, the sensors project from the carrier 56 by this wall thickness of the body 54. The carrier has circuit traces 58 through which the discrete sensors 44–51 are connected to connecting points 60. Electric lines extending through the inner hollow or, in an alternative, outside along the rod-shaped crosspiece 24 into the hollow space 26 of the external portion 20, are connected to these connecting points 60. The connecting points 60 are provided in the number required by the sensors for performing the function, they are eight in the exemplary embodiment if the sensors are electrodes and at least ten if the signal is acquired via electrically operated pressure elements.

The inner part 52 may be manufactured in several different ways. As shown in the FIGS. 6–8, the inner part 52 may be a cast plastic part that is already configured to form all the sensors 44–51, electrodes in this case, including their surfaces. This plastic part is now completely coated with a conductive coating, for example by electroplating. The metallic electrodes are also formed as a result thereof. In a further step, partition lines are etched, they are for example cut out with a laser so that the electrodes are separated, one electrode being connected to but one connecting point 60. Put another way, the electrodes and the connecting points 60 are insulated against each other so that the desired conductor connections are preserved.

The method of manufacturing an introitus probe, more specifically a vaginal probe, just described is suited for any probe, not only for the probe in accordance with claim 1. The applicant makes the right of filing a divisional application for manufacturing such a probe a proviso. The method steps are the following: manufacturing a plastic part in the form of what will later be the probe, coating said plastic part with a conductive coating, more specifically by electroplating. Forming partition lines in the coating for separating and defining electrodes so that one electrode is connected to at least one connecting point.

In another embodiment, the discrete sensors 44–51, electrodes in this case as well, are made from flat stampings of metal, such as medical grade special steel, and deposited onto a plastic carrier. They are directly connected via discrete conductors so that connecting points 60 are not necessary. In an improved embodiment, these metallic electrodes are bowl-shaped, meaning they have a rim that projects downward toward the carrier 56 only. The carrier 56 has channels mating with the rims of the electrodes engaging therein.

In another embodiment, a sheet metal blank is stamped or formed in such a manner that it forms all the sensors 44–51, electrodes again. It is then coated e.g., filled, with plastic. Next, material of the sheet metal blank is removed e.g., with a laser so that the electrodes and their supply lines are separated from each other.

The sensors 44–51 are for example pressure sensitive membranes or electronic pressure elements, preferably combined with metallic electrodes that are disposed on their outer surface. They are integrated in the surface of the vaginal probe so as to provide a form-positive fit therewith. In the combined implementation, each sensor must be supplied, besides the measuring line, by two supply lines, only two of which must lead to the electronics unit in the external portion 20. Each sensor e.g., the sensor 44, can be used for reference pressure.

Figure 9:
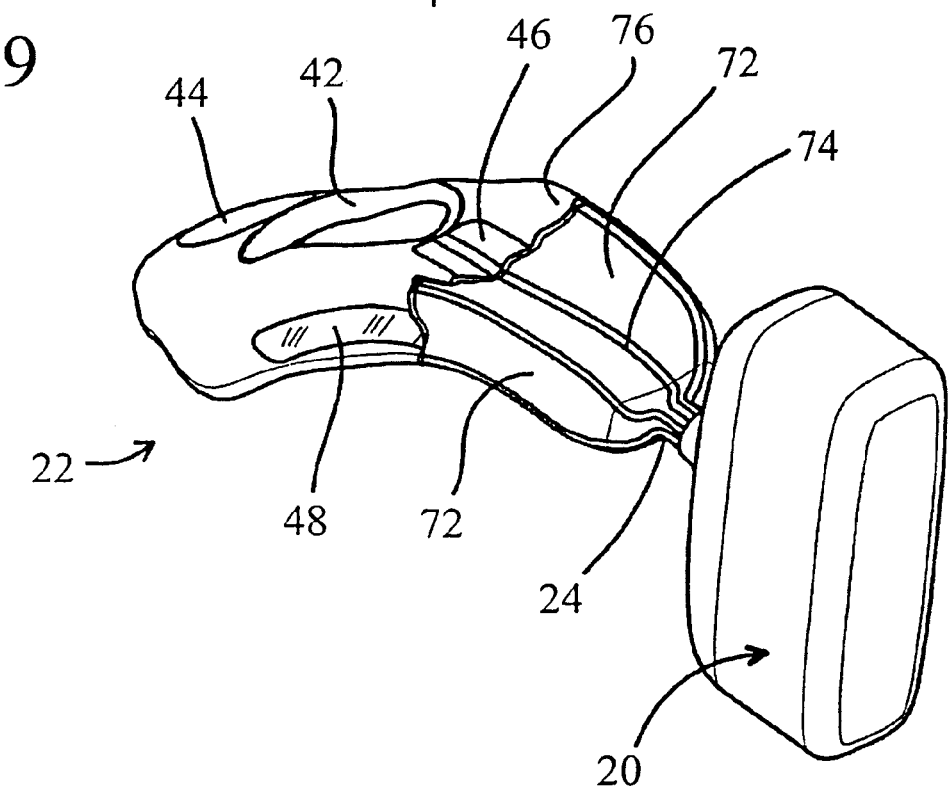
FIG. 9 is a partial sectional perspective view illustrating a vaginal probe in accordance with another embodiment.

FIG. 9 shows another exemplary embodiment the manufacturing of which is particularly advantageous. A preferably single piece molded body already having the shape of the finished probe is first produced. It forms in one piece the internal portion 22 and the crosspiece 24. At the end of the crosspiece it advantageously has a connection piece for connection with the external portion 20. Thin electric conductor areas 72 are deposited onto this molded body. The entire molded body is for example electroplated e.g., chromium plated. Partition lines are then made using a laser, meaning the discrete conductor areas are formed and electrically separated from each other. The conductor areas have in any case a conductor region on the crosspiece 24 so that they may be contacted at the end of the crosspiece i.e., from the external portion 20. The conductor areas 72 are preferably larger than the areas required for the sensors 44–51, they are not allowed to be smaller though. An externally surrounding layer 76 of electrically insulating material, more specifically a varnish layer, covers the conductor areas 72 and the areas exposed by the laser, but does not cover the areas of the sensors 44–51 which remain bare. As a result, the sensors are freely accessible from the outside. This layer 76 is only illustrated in parts in FIG. 9. In the front subsection 36, it is shown completely, in the rear subsection 40 it has been removed for showing the conductor areas 72 and the partition lines 74. The conductor areas 72 located side by side that can be seen in the upper portion of FIG. 9 are connected to the urethra electrodes 46 or form these in parts, respectively.

In still another embodiment the sensors 44–51 are formed by pressure sensitive membranes or electronic pressure elements that carry the electrodes on their surface and are integrated into the surface of the vaginal probe so as to provide a form-positive fit therewith. In this implementation, each sensor must be supplied, besides the measuring line, by two supply lines, only two of which must lead to the electronics unit in the external portion 20. The sensor 44 can be used as a reference pressure.

Continence can also be produced by mechanical weight load. Preferably, the weight of the internal portion 22 can be varied by suited means, for example by filling hollow spaces or by adding weights. The centroid is preferably provided in proximity to the urethra, meaning of the concave groove 53.

FIG. 1 still illustrates a separate control apparatus 78 to a much reduced scale. It has a corresponding emitter and receiver and the processing electronics unit 28 and display means 80.

The invention claimed is:

1. A vaginal probe, more specifically for diagnostis and therapy of incontinence, with an external portion, an internal portion, and a crosspiece joining said external and internal portions together, said external portion being configured to be a handle and said internal portion being configured as a generally rounded body, wherein said internal portion
   a) is oriented symmetrically about a longitudinal center plane which is oriented between the legs of the female patient when the vaginal probe is inserted,
   b) shows cross sections taken in planes running crossways to said longitudinal center plane and said crosspiece, wherein in said cross sections, a height dimension H, which is determined parallel to the longitudinal center plane, is at most half a width B, which is determined across said longitudinal center plane, and
   c) comprises a front subsection distal from the external portion, a central section and a rear subsection, the central section being curved, the rear subsection being connected to the crosspiece, said front subsection and said rear subsection being integrally joined together through the central section and said front subsection and said rear subsection being inclined to each other at an angle of 170–100°,
   wherein said internal portion comprises sensors on its surface.

2. The vaginal probe in accordance with claim 1, wherein the length of the internal portion of the vaginal probe is at least 75 mm.

3. The vaginal probe in accordance with claim 1, wherein the external portion forms an abutment face which is oriented transverse to the crosspiece and is large enough to prevent the external portion from being inserted into the vagina.

4. The vaginal probe in accordance with claim 1, wherein the vaginal probe is tapered in the region of the crosspiece.

5. The vaginal probe in accordance with claim 1, further comprising a processing electronics unit, wherein the sensors are connected to the processing electronics unit and are configured to be electrically conductive areas and/or pressure sensitive areas.

6. The vaginal probe in accordance with claim 1, wherein the external portion accommodates an emitter and a receiver for electromagnetic waves and that a separate control apparatus having a corresponding emitter and receiver and comprising display means for the recorded measurement signals is provided.

7. The vaginal probe in accordance with claim 1, wherein the internal portion and the crosspiece form a single piece molded body, wherein thin electrical conductor areas are deposited on said molded body, one conductor area being provided for each sensor, and wherein an external, surrounding layer of electrically insulating material is provided, said insullating material layer covering the molded body and the conductor areas so that only the areas intended for the sensors remain uncovered and the sensors remain freely accessible from the outside.

8. The vaginal probe in accordance with claim 1, wherein a concave groove that is symmetrical about the longitudinal center plane is provided in the rear subsection.

9. The vaginal probe in accordance with claim 1, wherein internal portion has, in the region of the rear subsection and of the central section, a left hand side and a right hand side lateral arched cavity.

10. The vaginal probe in accordance with claim 1, wherein the internal portion comprises, in its central section and/or in its front subsection, a recess having an area that is smaller than half the overall area defining the outer contour of said internal portion as viewed from the top.

11. The vaginal probe in accordance with claim 1, wherein the vaginal probe has, in the region of said crosspiece, a cross sectional area that is at most one third of the cross sectional area of the other two portions.

12. The vaginal probe in accordance with claim 1, wherein the vaginal probe has, in the region of said crosspiece, a cross sectional area that is at most 10% of the cross sectional area of the other two portions.

13. The vaginal probe in accordance with claim 1, wherein the internal portion and the crosspiece form a single piece molded body, wherein thin electrical conductor areas are deposited on said molded body, one conductor are being provided for each sensor, and wherein an external, surrounding layer of electrically insulating material in the form of a varnish layer is provided, said varnish layer covering the molded body and the conductor areas so that only the areas intended for the sensors remain uncovered and the sensors remain freely accessible from the outside.

* * * * *